United States Patent [19]
White et al.

[11] Patent Number: 6,129,935
[45] Date of Patent: Oct. 10, 2000

[54] METHODS FOR REARING INSECTS, MITES, AND OTHER BENEFICIAL ORGANISMS

[75] Inventors: James H. White; Lynda A. Stauffer, both of Gainesville; Kimberly A. Gallagher, Bronson, all of Fla.

[73] Assignee: Entomos, LLC, Gainesville, Fla.

[21] Appl. No.: 09/079,494

[22] Filed: May 15, 1998

[51] Int. Cl.$^7$ .............................. A01K 29/00; A23D 7/00
[52] U.S. Cl. .............................. 426/2; 426/602; 426/613; 426/635; 119/6.5
[58] Field of Search .............................. 426/2, 602, 635, 426/613; 119/6.5

[56] References Cited

U.S. PATENT DOCUMENTS

| | | | |
|---|---|---|---|
| 4,217,367 | 8/1980 | Hawley | 426/2 |
| 5,023,183 | 6/1991 | Friedman et al. | 435/373 |
| 5,728,573 | 3/1998 | Sugiura et al. | 435/254.1 |
| 5,799,607 | 9/1998 | Greany et al. | 119/6.5 |
| 5,899,168 | 5/1999 | Rojas et al. | 119/6.5 |

FOREIGN PATENT DOCUMENTS

| | | |
|---|---|---|
| 8040817 | 7/1994 | Japan . |
| 9628540 | 9/1996 | WIPO . |
| 9807335 | 2/1998 | WIPO . |

OTHER PUBLICATIONS

Kennett, C.E. and J. Hamai (1980) "Oviposition And Development In Predaceous Mites Fed With Artificial And Natural Diets (ACARI:Phytoseiidae)" Ent. exp. & appl. 28:116–122.

McMurtry, J.A. and J.G. Rodriguez In: Nutritional Ecology of Phytoseiid Mites, Chapter 19, pp. 609–644.

Rodriguez, J.G. and L.D. Rodriguez In: Nutritional Ecology of Phytoseiid Mites, Chapter 5, pp. 177–208.

Reinecke, John P. (1985) In. Comprehensive Insect Physiology Biochemistry and Pharmacology, Kerkut and Gilbert, ed., vol. 4, Chapter 9, pp 391–419.

Singh, Pritam In: Artificial Diets For Insects, Mites, and Spiders, Department of Scientific and Industrial Research, Auckland, New Zealand, pp 1–21.

McMurtry, J.A. and G.T. Scriven (1966) "Effects of Artificial Foods on Reproduction and Development of Four Species of Phytoseiid Mites" Annals Entomol. Soc. Amer. 59:267–269.

Ochieng, R.S., G.W. Oloo, E.O. Amboga (1987) "An Artificial Diet for Rearing the Phytoseiid Mite, *Amblyseius teke* Pritchard and Baker" Experimental & Applied Acarology 3:169–173.

Gilstrap, F.E. (1977) "Table–top production of tetranychid mites (Acarina) and their phytoseiid natural enemies" *J. Kan. Entomol. Soc.* 50:229–233.

Shehata, K.K. and Ludevit Weismann (1972) "Rearing The Predacious Mite Phytoseiulus Persimilis Athias–Henriot On Artificial Diet (Acarina: Phytoseiidae)" Biologia (Bratislava) 27(8):609–615.

Hanna, Makram A., and Edwin T. Hibbs (1970) "Feeding Phytophagous Mites on Liquid Formulations" Journal of Economic Entomology 63(5):1672–1674.

Atallah, Y. H. and L.D. Newsom (1966) "Ecological and Nutritional Studies on *Coleomegilla maculata* De Geer (Coleoptera: Coccinellidae). I. The Development of an Artificial Diet and a Laboratory Rearing Technique" Journal of Economic Entomology 59(5):1173–1179.

Smith, B.C. (1965) "Effects of Food on the Longevity, Fecundity, and Development of Adult Coccinellids (Coleoptera: Coccinellidae)" The Canadian Entomologist 97:910–919.

Vanderzant, E.S. (1969) "An Artificial Diet for Larvae and Adults of *Chrysopa carnea,* an Insect Predator of Crop Pests" Journal of Economic Entomology 62:256–257.

Wesson, Lawrence G. (1932) "Scientific Apparatus And Laboratory Methods" Science 75:339–340.

*Primary Examiner*—Nina Bhat
*Attorney, Agent, or Firm*—Saliwanchik, Lloyd & Saliwanchik

[57] ABSTRACT

The subject invention provides artificial diet compositions for rearing mites, insects, and other beneficial organisms. These artificial diets are particularly advantageous because they make it possible to raise organisms efficiently and economically.

5 Claims, No Drawings

METHODS FOR REARING INSECTS, MITES, AND OTHER BENEFICIAL ORGANISMS

BACKGROUND OF THE INVENTION

Crop producers face increasingly complex decisions in choosing strategies for protecting the value of their crops. Failure to protect the crop from damage caused by pests can have catastrophic consequences, resulting in an economic loss to growers and higher prices for consumers. Reliance on traditional chemical pesticides to protect the crop has a variety of disadvantages including health and environmental problems, and pest resistance.

Society places a very high value on the environment and on the safety of the food supply. In his nationally broadcast speech at the Democratic National Convention Aug. 29, 1996, President Clinton praised recently passed legislation aimed at reducing pesticide residue in the food supply. The presence of this issue in such an important policy speech reflects the widespread desire to reduce pesticide residue. This increased demand for lower pesticide residues and the concomitant desire to reduce nontarget effects of pesticides has resulted in significantly fewer pesticides being under registration for use. Some of the most harmful pesticides have lost registration due to EPA action, some have been voluntarily withdrawn (such as propargite on several crops) and others have been allowed to lapse rather than being re-registered. The net impact of these pressures is that fewer pesticides are now available for legal use on crops.

With only a few legal pesticides available for use on each crop, pest resistance becomes another concern for the growers. Repeated use of a single pesticide, especially against pests with multiple generations in a single growing season, is the outdoor equivalent of a laboratory experiment aimed at developing an insect strain resistant to the pesticide. The same result occurs outdoors as in the laboratory experiment, and resistant insects begin to appear, often increasing their populations very rapidly once resistance to the maximum applied insecticide rate is achieved. In the past, when resistance began to occur, growers simply could turn to pesticides with different active ingredients to restore control of the pest. With fewer pesticides available, and with the appearance of many insects which are now resistant to multiple pesticide types, growers can be forced to watch helplessly as their crops are destroyed. This has been the case recently in the Imperial Valley of California with the multiply resistant sweet potato whitefly.

Integrated Pest Management, or IPM, has been developed as a tool to increase the efficiency of pesticide use. Rather than applying the pesticide according to a recommended schedule, growers now rely on thorough scouting of the crop to determine the identity, location and relative number of pests. Armed with this information, growers can apply pesticides only where they are needed and only if the pest pressure is likely to cause economic harm if left untreated. IPM results in decreased overall pesticide use, which results in lower food residues and fewer non-target effects. The biological benefit of IPM is that decreased pesticide usage and the tolerance of low levels of pests conserves natural enemies such as predators, parasites and parasitoids which can aid in control of pests. These natural enemies often are more sensitive than the pests and present at lower levels than the pests, meaning that they often are totally eliminated from the crop system under a program of indiscriminate spraying.

Economic forces stand in the way of the natural extension of IPM to include the mass rearing and intentional release of natural enemies to provide increased control of pests. Although many beneficial arthropods have been identified and laboratory scale work has indicated promise for their use in such a program, their implementation in IPM has been minimal. Indeed, biological agents in general account only for about 1% of pesticide sales.

The primary factor preventing wider employment of natural enemies in IPM is the cost of the natural enemies. The most successful biological pesticide, *Bacillus thuringiensis,* is successful because it can be produced at very low cost in large scale bacterial fermenters and subsequently sold at prices competitive with traditional pesticides used to control the same lepidopterous pests. However, the second most successful biological agent, *Phytoseiulus persimilis,* is sold at about ten to twenty times the cost of chemical pesticides used to control the two spotted spider mite. At this time *P. persimilis* is used only on very high value crops: strawberries, greenhouse vegetables and nurseries. These high value niche markets have no other effective legal pesticides capable of controlling the two spotted spider mite. Only when the cost of P. persimilis can be reduced to the level of chemical alternatives can it be expected to compete on other, larger crops such as corn, where its efficacy already has been demonstrated.

*P. persimilis* and other natural enemies besides those produced in fermenters are too expensive for use on most crops because of the high cost of producing them. In most cases, these natural enemies are grown on prey or host insects which must first be reared, often on a host plant. This process is very labor intensive and space intensive. Replacement of the prey or host with an artificial diet and development of associated mass production technology with decreased labor inputs could bring these costs down dramatically.

The principal phytoseiid mites which are commercially available at this time are *Phytoseiulus persimilis, Metaseiulus occidentalis* and *Amblyseius cucumeris.* Of these, *M. occidentalis* and *P. persimilis* are obligate predators when in their natural habitat, consuming only prey. *A. cucumeris,* on the other hand, consumes both prey (thrips rather than spider mites in this case) and pollen encountered on plant surfaces. Both *M. occidentalis* and *P. persimilis* are very efficient predators of spider mites. *P. persimilis* currently accounts for most predatory mite sales worldwide.

In the laboratory, neither *M. occidentalis* nor *P. persimilis* has been cultured in the absence of prey (see Kennett, C. E. and J. Hamai, (1980) "Oviposition and development in predacious mites fed with artificial and natural diets (Acari: Phytoseiidae)" *Ent. Exp. Appl.* 28:116–122, for example). Instead, a plant is grown and infested with spider mites. Predator mites are then released to feed on the spider mites (Gilstrap, F. E. (1977) "Table-top production of tetranychid mites (Acarina) and their phytoseiid natural enemies" *J. Kan. Entomol. Soc.* 50:229–233). This three component system of plant, pest and predator is the basis for commercial production of *M. occidentalis* and *P. persimilis.* Separate facilities are usually maintained for each of the three components of the system, adding significantly to production costs.

An additional large cost component for conventionally grown *P. persimilis* is that these mites must be packaged for transportation and application to the crop in the absence of food, since this food is a pest. Thus, it is not possible to store mites ready for shipping for extended periods. The result of this is that it is standard practice to overproduce *P. persimilis* by as much as 50% of anticipated demand, so that surges in demand can be met.

The nutritional requirements of mites have been studied. See, for example, J. A. McMurtry and J. G. Rodriguez (Nutritional Ecology of Phytoseiid Mites, Chapter 19, pp 609–644) and J. G. Rodriguez and L. D. Rodriguez (Nutritional Ecology of Phytoseiid Mites, Chapter 5, pp 177–208). Also, various attempts have been made to develop artificial diets for mites and other organisms. See, for example, Reinecke (Nutrition: Artificial Diets, Chapter 9, pp 391–419, In: *Comprehensive Insect Physiology Biochemistry and Pharmacology,* Kerkut and Gilbert, ed. (1985), Vol. 4) and Singh (Artificial Diets For Insects, Mites, and Spiders, Department of Scientific and Industrial Research, Auckland, New Zealand, pp 1–21). Diets specifically designed for mites are described in McMutry and Scriven (Effects of Artificial Foods on Reproduction and Development of Four Species of Phytoseiid Mites (1966) *Annals Entomol. Soc. Amer.* 59:267–269); Shehata and Weismann ("Rearing The Predacious Mite Phytoseiulus Persimilis Athias-Henriot On Artificial Diet" (1972) Biologia (Bratislava) 27(8):609–615); Ochieng et al. ("An Artificial Diet For Rearing the Phytoseiid Mite, *Amblyseius teke* Pritchard and Baker" (1987) *Experimental & Applied Acarology* 3:169–173); Hanna and Hibbs ("Feeding Phytophagous Mites on Liquid Formulations" (1970) *Journal of Economic Entomology* 63(5): 1672–1674). Diets for insects such as coleopterans have also been described (Atallah and Newsom (1966) "Ecological and Nutritional Studies on Coleomegilla maculata De Geer (Coleoptera: Coccinellidae). I. The Development of an Artificial Diet and a Laboratory Rearing Technique" *Journal of Economic Entomology* 59(5):1173–1179; Smith (1965) "Effects of Food on the Longevity, Fecundity, and Development of Adult Coccinellids (Coleoptera: Coccinellidae)" *The Canadian Entomologist* 97:910–919; and Vanderzant (1969) "An Artificial Diet for Larvae and Adults of Chrysopa carnea, an Insect Predator of Crop Pests" *Journal of Economic Entomology* 62:256–257). There has been no report of a low cost diet for effectively raising Phytoseiid mites.

An artificial diet with associated low cost mass production technology and equipment for *P. persimilis* and other phytoseiid mites would revolutionize their production while providing an opportunity to greatly increase use of these predators. Cost-effective release of inundative amounts of phytoseiids has the potential for dramatically reducing use of conventional insecticides without increased crop loss. Lower costs for phytoseiids also should increase the range of crops on which these predators could be components of IPM programs.

BRIEF SUMMARY OF THE INVENTION

The subject invention concerns materials and methods useful for rearing insects, mites, and other beneficial organisms. In a preferred embodiment, the subject invention provides an artificial diet for predatory and/or parasitic insects and mites. In a specific embodiment, the subject invention provides a unique and advantageous artificial diet for growing phytoseiid mites. This diet is a low cost diet which can be used, advantageously, to grow large numbers of phytoseiid mites. Also, the subject invention eliminates or reduces the need to include prey or host material in the diet of beneficial organisms. Thus, this invention overcomes some of the key economic obstacles in the use of phytoseiid mites in a pest control program.

In a preferred embodiment, the novel diet of the subject invention comprises a source of fat, a source of amino acids, at least one intact protein, and a carbohydrate source all in an aqueous solution. In a preferred embodiment of the subject invention, dried egg yolk provides the fat, a meat-based hydrolysate provides amino acids, the intact protein is a plant protein, and the carbohydrate is maltose. In a specific embodiment the meat-based hydrolysate is Primatone and the plant protein is soy flour. The artificial diet of the subject invention may, optionally, comprise further components including for example a lipid supplement, an antibiotic, and/or vitamins.

The subject invention concerns not only the artificial diet but also the use of the diet to rear desired insects and/or mites in large numbers at a low cost.

DETAILED DISCLOSURE OF THE INVENTION

The subject invention provides a growth medium which can be used to grow commercial quantities of mites or insects at a low cost. In a specific embodiment, the diet can be used to grow phytoseiid mites. Thus, for the first time, phytoseiid mites can be made available for pest management at an economically feasible low cost.

The artificial diet of the subject invention comprises a source of fat, a source of amino acids, at least one intact protein, and a carbohydrate source all in an aqueous solution. Sources of fat which can be used according to the subject invention include egg yolk and other compositions having an emulsified fat component. In a preferred embodiment, dried egg yolk serves as the source of the fat. Egg yolk is particularly preferred because it serves as an additional source of protein and other nutrients in addition to providing emulsified fat.

As used herein, reference to a source of amino acids refers to amino acids which are not in the form of an intact protein. These amino acids are also referred to herein as free amino acids and include individual amino acids and/or short peptides such as those which are present in protein hydrolysates. Thus, the source of amino acids can be, for example, a protein hydrolysate. Protein hydrolysates are commercially available and/or can be readily prepared by those skilled in the art. Examples of suitable hydrolysates include casein enzymatic hydrolysate, yeast extract, and lactalbumin enzymatic hydrolysate. Preferably, the source of amino acids is a meat-based hydrolysate. In a specific embodiment the hydrolysate can be Primatone or Primatone RL which are available from Sheffield Products Division of Quest International, Hoffman Estates, Ill.

The intact protein used according to the subject invention can be a plant or animal protein. In a preferred embodiment the intact protein is a plant protein. Proteins which can be used according to the subject invention include but are not limited to soy flour, wheat germ, and corn meal. In a specific embodiment the plant protein is soy flour.

The carbohydrate source used in the artificial diet of the subject invention may be a composition such as honey which contains a mixture of carbohydrates or it may be a single carbohydrate. Preferred carbohydrates are maltose, cornstarch, and glycogen.

In a preferred embodiment of the subject invention the osmotic pressure of the composition is kept above about 150 mOsm. Preferably the osmotic pressure is between about 175 mOsm and about 1200 mOsm. Most preferably the osmotic pressure is between about 200 mOsm and about 450 mOsm.

In formulating the artificial diet of the subject invention it is preferable for the dried egg yolk and the intact protein to be present in relatively large amounts and to be present in roughly equal amounts. The source of amino acids should be present in much lower amounts and can be, for example, present at about 0.1–20% of the amount (by weight) of the intact protein. More preferably the amino acid should be present at about 0.5–10% of the intact protein. Particularly good results have been obtained with the source of amino acids present at about 1% of the intact protein. Thus, the ratio of intact protein to free amino acids is, by weight, between about 1000:1 and about 5:1. More preferably this ratio is between about 100:1 and about 10:1. The carbohydrate is also present in a relatively low amount and can be, for example, about 5–10% of the amount of the intact protein.

The concentration of the ingredients can be manipulated to achieve a desired osmotic strength.

In one embodiment of the invention, the diet can be supplemented with one or more vitamins. The vitamin(s) used may be, for example, vitamin E, vitamin C, choline, folic acid, pantothenic, acid and vitamin B12.

In a further embodiment of the subject invention the diet contains salts such as Wesson's salts (Wesson, L. G. (1932) "A Modification of the Osborne-Mende Salt Mixture Containing Only Inorganic Constituents" *Science* 75:339–340). These salts may, advantageously, include phosphate salts.

In addition to use in rearing mites, the diet of the subject invention can be used for rearing beneficial insects such as predaceous and parasitic insects. Such insects include, but are not limited to, insects from the orders Hemiptera, Hymenoptera, Coleoptera, Diptera, Heteroptera and Neuroptera. Examples of specific insects are *Geocoris punctipes, Podisus maculiventris,* Orius spp. *Perillus bioculatus, Lyctocoris campestris* and *Xylocoris flavipes,* all hemipterans; *Calosoma sycophanta, Hippodamia convergens,* and *Colemegilla maculata;* coleopterans; and *Diapetimorpha introita, Catolccus grandis* and *Cryptus albitarsus;* hymenopterans. The diet of the subject invention can be administered to the mites or insects through a variety of techniques known to those skilled in the art. In one embodiment arenas can be constructed from tightly sealed, vented Falcon number 1006 50 mm Petri dishes. A vent is constructed by drilling a large hole in the lid of the dish and covering the hole with fine nylon mesh welded onto the outer surface of the lid. These arenas are held in a plastic box humidified with beakers of water or saturated salt solution and placed into the incubator in a sealed plastic bag to ensure equilibration of the air in the arenas with the humidity control solution.

Mite harborage and oviposition sites can be provided within the arena by supplying open cell foam material with openings of approximately 400 to 800 microns. For procedures where the number of mites and eggs is to be quantified, this foam material can be sliced into very thin sections of one layer of foam "cells" on a microtome so that all surfaces of the material can be examined thoroughly through the dissecting microscope. This foam can be anchored to the arena floor with a small piece of "Tac n Stik" adhesive. The diet can be enclosed within a film dome. The film can be, for example, Parafilm™.

Alternate films to Parafilm can also be used. For example, Polycarbonate Track-Etched Membranes (PCTE) can be used. These membranes are extremely thin (about 6 microns). In contrast to traditional filter membranes which remove particles by forcing them to travel through a tortuous path, the membranes have pores which bore straight through the membrane. These membranes have pore openings of sufficient size to allow feeding by mites without the need to physically pierce a tough film. Encapsulation of diet into alginate beads and carboxymethylcellulose beads can also be done.

Following is an example which illustrates procedures for practicing the invention. This example should not be construed as limiting. All percentages are by weight and all solvent mixture proportions are by volume unless otherwise noted.

EXAMPLE 1

Production of *A. cucumeris*

*A. cucumeris* can be obtained from Novartis BCM. The artificial diet, as described above, is mixed in a blender.

A specific diet useful according to the subject invention consists essentially of the following nutrients:

| Nutrient | Amount (grams) |
|---|---|
| Primatone | 0.25 |
| Soy flour | 2.5 |
| Egg Yolk (dried) | 2.5 |
| Maltose | 1.25 |
| Water | 43.5 |

Several adults are added to each dish. The inoculated Petri dishes are incubated at about 26 C, for about 16 hr in the light and about 8 hr in the dark to produce abundant amounts of *A. cucumeris*.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for rearing a predatory insect or predatory mite wherein said method comprises feeding said insect or mite a composition wherein said composition comprises fat, free amino acids, at least one intact protein, and a carbohydrate, wherein the ratio of intact protein to free amino acids is by weight, at least about 5:1.

2. The method, according to claim 1, wherein said mite is a phytoseiid mite.

3. The method, according to claim 1, wherein said insect is selected from the group consisting of *Coleomegilla maculata* and *Hippodamia convergens*.

4. The method, according to claim 1, wherein said insect is a *Geocoris punctipes*.

5. The method, according to claim 1, wherein said insect is an Orius spp.

* * * * *